(12) United States Patent
Kretschmann

(10) Patent No.: US 9,283,292 B2
(45) Date of Patent: Mar. 15, 2016

(54) DEVICE FOR USE IN A MEDICAL TREATMENT ROOM

(71) Applicant: Dräger Medical GmbH, Lübeck (DE)

(72) Inventor: Hanno Kretschmann, Hamburg (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

(21) Appl. No.: 14/404,098

(22) PCT Filed: May 31, 2013

(86) PCT No.: PCT/EP2013/061254
§ 371 (c)(1),
(2) Date: Nov. 26, 2014

(87) PCT Pub. No.: WO2013/178781
PCT Pub. Date: Dec. 5, 2013

(65) Prior Publication Data
US 2015/0129781 A1    May 14, 2015

(30) Foreign Application Priority Data
May 31, 2012    (DE) .......................... 10 2012 010 676

(51) Int. Cl.
*A61L 2/10* (2006.01)
*A61L 2/08* (2006.01)
*A61B 19/00* (2006.01)
*F21V 21/40* (2006.01)

(52) U.S. Cl.
CPC . *A61L 2/10* (2013.01); *A61L 2/084* (2013.01); *A61B 19/5202* (2013.01); *F21V 21/403* (2013.01)

(58) Field of Classification Search
USPC .............. 250/453.11, 454.11, 455.11, 504 R, 250/504 H
See application file for complete search history.

(56) References Cited

U.S. PATENT DOCUMENTS

| 8,686,963 B2 | 4/2014 | Rolus Borgward |
| 2007/0138966 A1 | 6/2007 | Marka et al. |
| 2009/0227847 A1 | 9/2009 | Tepper et al. |
| 2010/0246169 A1 | 9/2010 | Anderson et al. |

(Continued)

FOREIGN PATENT DOCUMENTS

| EP | 2 287 747 A1 | 2/2011 |
| GB | 2 387 542 A | 10/2003 |
| KR | 2011 0089385 A | 8/2011 |

(Continued)

OTHER PUBLICATIONS

Wikipedia freie Enzyklopädie, Stichwort: Lichtfarbe, URL: http://de.wikipedia.org/wiki/Lichtfarber [recherchiert am Feb. 22, 2013].

*Primary Examiner* — Nicole Ippolito
(74) *Attorney, Agent, or Firm* — McGlew and Tuttle, P.C.

(57) ABSTRACT

A device (1; 26) for use in a medical treatment room includes at least one control unit (2, 6; 18) designed as a light guide and at least one light source (3, 3'; 21) which emits light with a wavelength between 380 nanometers and 420 nanometers, particularly 405 nanometers, and is arranged in such a manner that emitted light is coupled into the light guide. The light guide is designed in such a manner that light exiting the light guide again at least partially illuminates the surface of the control unit (2, 6; 18).

22 Claims, 3 Drawing Sheets

(56) References Cited

U.S. PATENT DOCUMENTS

Figure 1:
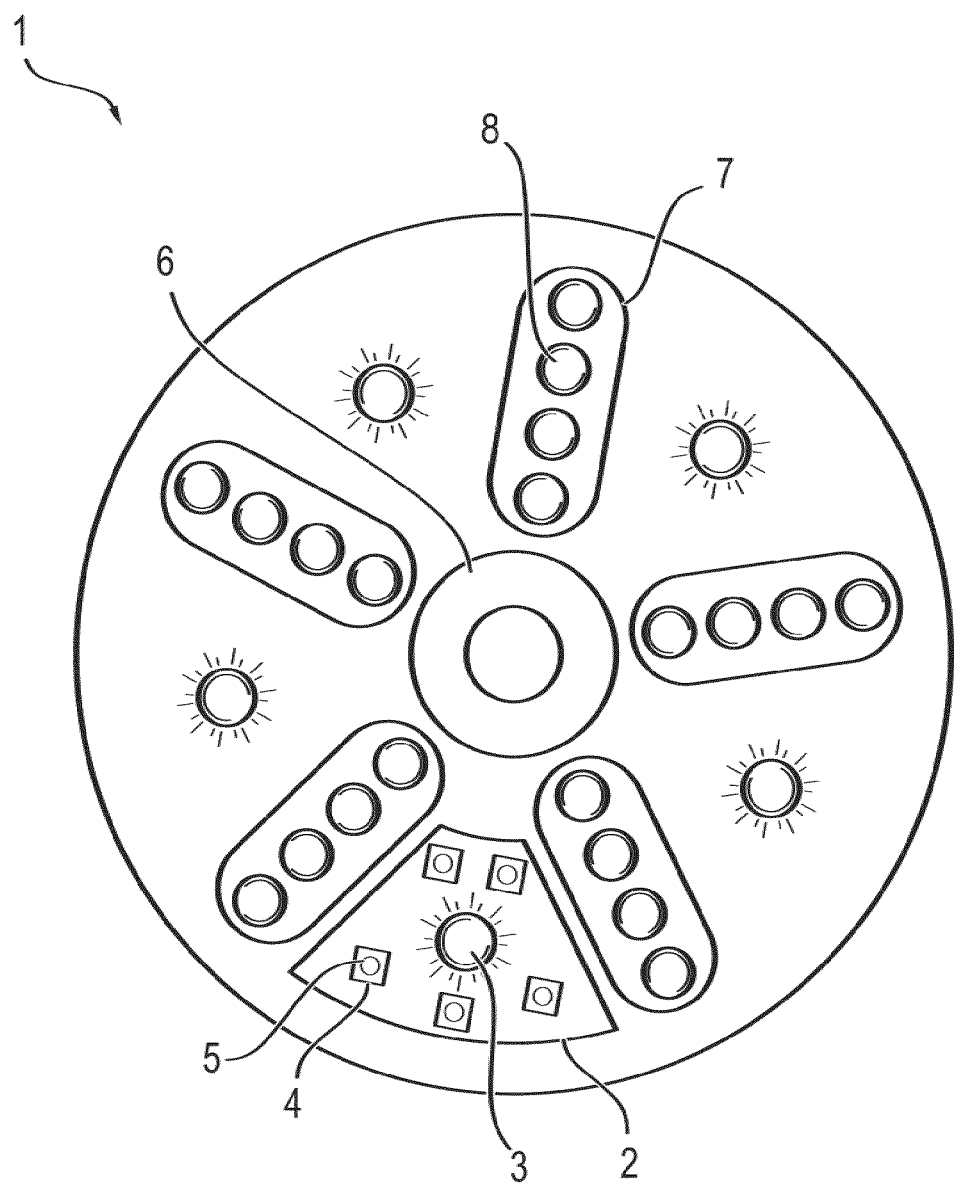

2011/0085936 A1  4/2011  Haytman et al.
2014/0034849 A1* 2/2014  Lyslo .................. A61L 2/10
                                                250/492.1

FOREIGN PATENT DOCUMENTS

| WO | 99/50593 A2 | 10/1999 |
| WO | 2007/012875 A1 | 2/2007 |
| WO | 2009/056838 A1 | 5/2009 |

* cited by examiner

DEVICE FOR USE IN A MEDICAL TREATMENT ROOM

The present invention pertains to a device for use in a medical treatment room, comprising at least one control unit.

Devices that are used, for example, to control and monitor vital functions of patients and/or to support a physician while performing treatments, are used in medical treatment rooms. In order for the devices to be able to be operated by a person, they have control units. A control unit is, for example, a handle, by means of which the device can be brought into a desired position or to a desired location. Furthermore, a control unit may be a switch or a switch panel with sensors, whose actuation leads to the activation or deactivation of operating states of the device.

Contamination with especially pathogenic bacteria may occur despite prior sterilization or disinfection of the surfaces of the control units. This may happen due to bacteria present on the hand of a person operating the device reaching the surface of the control unit during the operation of the device. This may, in turn, cause bacteria to reach the hands of other persons operating the device during the treatment of a patient, so that there is an increased risk for a patient being treated to come into contact with pathogenic bacteria. This risk is especially high in case of devices that are used in a sterile environment. For example, an operating room or a room in which a patient is under intensive care.

The basic object of the present invention is to propose an advantageous device for use in a medical treatment room, comprising a control unit, in which contamination of the control unit with pathogenic bacteria is hindered.

This object is accomplished with the device according to claim 1.

Advantageous embodiments and variants of the present invention are the subject of the dependent claims.

The device according to the present invention for use in a medical treatment room comprises at least one control unit designed as a light guide and at least one light source, which emits light with a wavelength between 380 nm and 420 nm, especially at 405 nm, and is arranged such that emitted light is coupled into the light guide, wherein the light guide is designed such that light exiting the light guide illuminates the surface of the control unit at least partially.

The inventor recognized that the effect of irradiation of pathogenic bacteria with visible light in the range of 400-500 nm, which is described in WO 2007/012875 A1, can be used to reduce or even prevent in the ideal case the contamination of the control unit with pathogenic bacteria by irradiating or penetrating by radiation a control unit of a device with light in this wavelength range. The device according to the present invention can therefore be used especially advantageously under sterile conditions, which must prevail in operating rooms or in rooms in which patients are under intensive care.

Due to the light source being a part of the device according to the present invention, i.e., due to the light source being arranged in or at the device, the light source can be arranged adjacent to the surface of the control unit, i.e., at a distance of a few cm or, for example, directly behind the surface by means of light guides, in such a way that, for example, one LED or even a plurality of LEDs with a total output of a few W can be used as the light source in order to reach an intensity of irradiation that brings about a significant reduction of pathogenic bacteria within a few seconds to minutes on a control unit with a surface area of, for example, 50 cm². The total output is, for example, in the range of 1 W to 10 W and the intensity of radiation on the surface of the control unit is between 0.1 W per cm² to 10 W per cm². A dose of about 50 J per cm² is needed to reduce the pathogenic bacteria by five orders of magnitude. This dose is reached in 250 sec in case of a surface area of, for example, 50 cm² and an output of 10 W irradiating or penetrating the surface.

If the surface of the control unit of the device according to the present invention is sterilized at first, it can be maintained in an essentially sterile state by the light source being left switched on after being touched by a person until a reduction of the batteries by, for example, five orders of magnitude is brought about. It is advantageous if the light source is switched on additionally while being touched.

Contrary to this, a considerably higher output of the light source is necessary for irradiating a surface with a separate light source arranged at a great distance from the surface, as it is described, for example, in WO 2009/056838 A1, to still reach a significant reduction of pathogenic bacteria at a distance of 1 m to 2 m from the irradiated surface. In addition, the light source described there requires more than 8 hours for achieving a significant reduction of pathogenic bacteria. An even higher output of the light source would be necessary for a shorter time.

A light guide is any body in which coupled light is reflected several times to and fro between the walls defining the body. The walls of the light guide may be designed such that the light is reflected only partially during each reflection, i.e., part of the light passes through the wall. In the simplest case, a light guide is a body, for example, one made of glass, acrylic glass or another plastic, from the said entire surface of which coupled light exits.

Light-guiding structures are advantageously formed and arranged in the light guide and/or on surfaces thereof in such a manner that coupled light is deflected in the direction of the surface of the control unit.

Then decoupling may be brought about by scattering structures distributed in the material of the light guide, by specific fine surface structures or by fine, printed patterns. These light-guiding structures cause coupled light to be guided preferably in the direction of the surface touched during the operation of the control unit by reflection, diffraction, refraction or scattering and then to be decoupled at least partially via the surface being touched during the operation. For example, light-guiding structures are Fresnel structures designed in the mm or μm range. The dimensions of diffractive structures may also be, in particular, in the nm range. The inhomogeneous distribution of the decoupling structures causes that a uniform, especially homogeneous transillumination of the surface is achieved even with only one light source coupled on one side.

Due to the control unit being designed as a light guide, it is sufficient to couple the light of the light source into the control unit on one side in order to transilluminate the entire surface of the control unit. Due to the fact that the light is not reflected completely within the control unit but exits at least partly via the surface being touched during the operation, this surface is transilluminated and pathogenic bacteria present thereon are killed. This effect may be facilitated by the light guide being designed such that light exits predominantly from the surface of the control unit that is being touched during the operation and light can exit to a low extent only or not at all from other surfaces of the control unit. This can be achieved, for example, by a suitable coating of the other surfaces.

An essentially homogeneous transillumination or illumination of the surface of the control unit, i.e., a homogeneous intensity distribution on the surface may also be brought about by applying additional structures, for example, in the form of varnishes, coatings or particles, to the surface. The extension of such structures may be in the nm, μm or even mm range.

The control unit is designed as a handle in one embodiment of the present invention.

As an alternative or in addition to the design as a handle, the control unit advantageously comprises at least one touch surface, which is in functional connection with a touch sensor and is designed and/or arranged such that the touch surface is transilluminated by the emitted light when the light source is activated.

The number of pathogenic bacteria can be reduced in this manner by killing or reduced to zero in the ideal case in a specific manner by the irradiation with light on the touch surfaces provided for touching by a person operating the device.

The control unit is advantageously manufactured from transparent plastic or from glass.

The control unit is advantageously designed as a touch-screen.

The device is a lighting fixture for an operating room in a preferred embodiment of the present invention.

Lighting fixtures for operating rooms may also be operated by the physician performing the surgery. He now touches control units, for example, handles and/or touch elements, especially touchscreens, which are arranged on the lighting fixture for the operating room, for example, at the edge outside the light cone of the lighting fixture for the operating room. The touch elements may, of course, also be integrated on the top side or underside of the lighting fixture for the operating room, especially in an edge area.

If the surgeon does not disinfect or sterilize his hands and/or does not put on new gloves during the surgery each time after touching control units of the lighting fixture for the operating room, it cannot be ruled out that pathogenic bacteria will reach the hands or gloves of the surgeon due to his touching the surfaces of these control units. As an alternative, the surgeon may also let staff present during the surgery touch control units of the lighting fixture for the operating room. However, he must give instructions for this repeatedly during the surgery. This is complicated and may possibly also compromise the surgeon's concentration. It is therefore necessary to kill pathogenic bacteria as effectively as possible and continuously on the surfaces of control units of a lighting fixture for an operating room, and this can be achieved by designing the lighting fixture for the operating room according to the present invention.

In an alternative embodiment, the device is a supply unit for connecting a medical device. Supply units are fastened on the ceiling, for example, by means of a movable arm system in operating rooms or treatment rooms and are used to connect medical devices, for example, anesthesia apparatuses, respirators or thermotherapy devices, for example, to a gas supply system and/or to electric energy. Supply units likewise have control units, which can be effectively protected from excessive contamination by pathogenic bacteria with light in the wavelength range between 380 nm and 420 nm by means of the arrangement according to the present invention of a light source.

Figure 2:
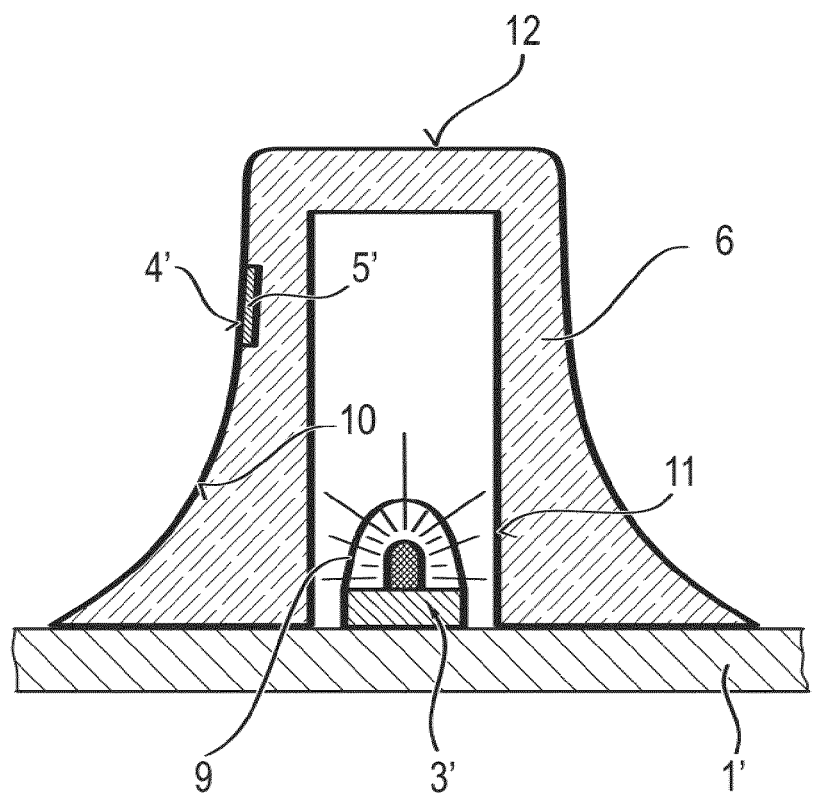
Figure 3:
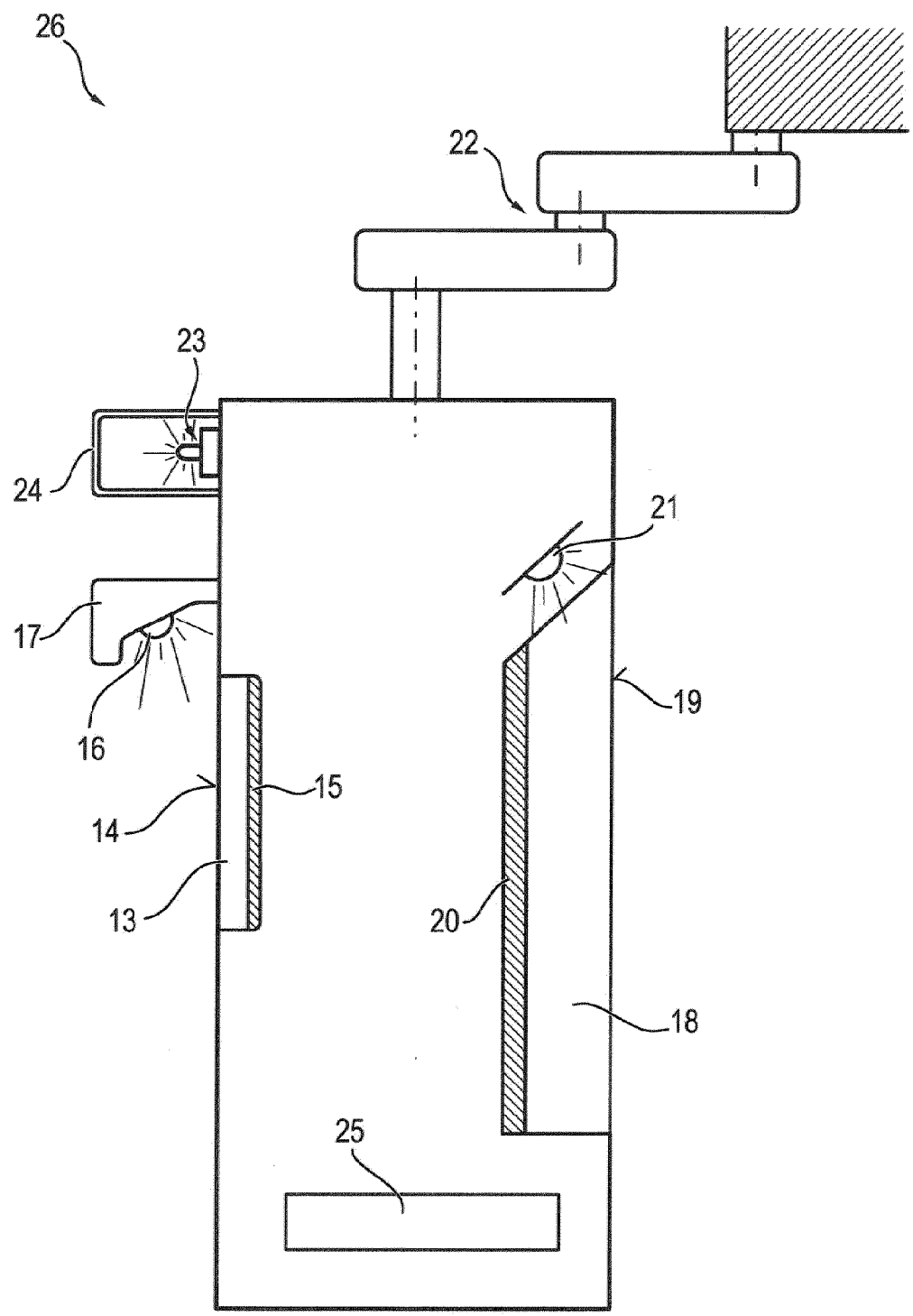

The present invention will be explained in more detail below on the basis of the exemplary embodiments shown in the figures. In the drawings, FIG. 1 shows a device according to the present invention in the form of a lighting fixture for an operating room, FIG. 2 shows a handle transilluminated with light for positioning and controlling the lighting fixture for an operating room according to FIG. 1, and FIG. 3 shows a supply unit for connecting a medical device.

Identical reference numbers in the figures designate identical objects.

FIG. 1 schematically shows a lighting fixture 1 for an operating room. A view at right angles to the part of the operating room lighting fixture 1 emitting the light for the surgery is shown. The beam path of the light is directed out of the drawing plane. To generate the light for the surgery, for example, six modules 7 with, for example, four lighting means 8 each are arranged, for example, in a star-shaped pattern around the center of the lighting fixture 1 for the operating room. The lighting means 8 are, for example, white LEDs, by means of which a region of an operation can be illuminated in the known manner. As an alternative, the lighting means 8 may also be formed from LEDs having different colors, gas discharge lamps, incandescent lamps and/or halogen lamps. Instead of in the form of modules, the lighting means 8 may, of course, also be arranged one by one in the lighting fixture 1 for the operating room. Only one nodule 7 and one lighting means 8 are provided with reference numbers for clarity's sake.

Furthermore, the lighting fixture 1 for the operating room has six light sources 3, of which only one is again provided with a reference number. The light sources 3 are, for example, LEDs or xenon lamps, which emit light in the range of 380 nm to 420 nm. However, light with a wavelength of 405 nm is preferably emitted. The LEDs may be designed for this such that the emitted spectrum is a narrow-band spectrum (for example, from 15 nm to 20 nm FWHM and has its maximum at 405 nm. The light sources 3 are directed such that when the lighting fixture 1 for the operating room is positioned above a wound area, the light emitted by the light sources 3 irradiates the wound space and areas located next to it, so that pathogenic bacteria present in the wound space as well as the surrounding area are killed. If the distance between the lighting fixture 1 for the operating room and the wound space is approx. 100 cm and the wound area is approx. 100 $cm^2$ to 300 $cm^2$, the light sources 3 are designed for this such that an intensity of radiation of 1-10 $W/m^2$ is present on the wound surface. In addition, an optical system, not shown, with which the light emitted by the light sources 3 can be focused onto the wound space and the surrounding area, may be provided. This optical system as well as the output of the light sources 3 and/or of the lighting means 8 can be controlled by actuating touch sensors 5 placed behind touchpads 4, The touchpads 4 and touch sensors 5 are provided on a control unit 2 designed as a touchscreen. The control unit 2 is made, for example, of glass, but it may also be made of transparent plastic. The control unit 2 is preferably part of a glass pane, not shown in FIG. 1, which covers the light sources and the lighting means 8, or is integrated in said glass pane.

One of the light sources 3 is arranged behind the control unit 2, so that light emitted by the light source 3 transilluminates the control unit 2 and thus also brings about the killing of pathogenic bacteria, which may be present on the surface of the control unit 2. The surface of the control unit is structured, for example, by a suitable coating, such that the intensity distribution of the light on the surface is essentially homogeneous.

The lighting fixture 1 for the operating room has, furthermore, a control unit 6, which is designed as a handle, which is arranged, for example, centrally in the area of the light emission area of the lighting fixture 1 for the operating room and is used to position the lighting fixture 1 for the operating room relative to a patient to be treated.

FIG. 2 schematically shows a section through the handle 6 according to FIG. 1. The section plane passes centrally through the handle 6 and is at right angles to the drawing plane of FIG. 1. The handle 6 is fastened on a surface 1' in the area of the light emission area of the lighting fixture 1 for the operating room. Fastening may be performed by screwing, bonding or according to other suitable methods. The handle 6 has a cavity, into which an additional light source 3' protrudes, which is not shown in FIG. 1 for clarity's sake. Just like the light source 3, the additional light source 3' emits light with a wavelength between 380 nm and 420 nm, especially at 405 nm. The additional light source 3' may have a design identical to that of the light sources 3 especially in terms of the radiation source and the emitted spectrum. An optical system 9, by means of which the light is radiated uniformly into the cavity, is arranged above the additional light source 3', so that light is reflected to and fro within the handle 6 designed as a light guide and consisting, for example, of transparent plastic and exits the handle 6 via the wall 10 and a wall 12. The surface of the handle 6 is transilluminated in this manner by light especially of a wavelength of 405 nm, and pathogenic bacteria present on the surface of the handle 6 are killed.

The wall 11 preferably has a surface structure, not shown in the figure, for example, an array of Fresnel structures designed in the mm or μm range, which are designed and arranged such that light coupled into the handle, which reaches the wall 11 after a reflection on the wall 10, is reflected back specifically in the direction of the wall 10 and exits there at least partially again. It is achieved hereby that the predominant majority of the surface of the handle that is touched during the operation is transilluminated and only a small part of the light coupled in, in the ideal case a part tending towards zero, will again enter the cavity.

The handle 6 has, furthermore, a touch surface 4' and a touch sensor 5', via which, for example, the focusing and/or the output of the lighting means 8, of the light sources 3 and/or of the additional light source 3' can be controlled.

As an alternative or in addition, the lighting fixture for the operating room may have at least one touchscreen, which is designed as a light guide made of glass or plastic and which is integrated, for example, in the top side or underside in an edge area of the lighting fixture for the operating room. Light of a light source emitting in the wavelength range of 380 nm to 420 nm, especially 405 nm, for example, of a light source 3, is coupled into the light guide. The light guide is designed here, for example, by a corresponding array of Fresnel structures designed in the mm or μm range or by scattering, reflecting, refractive or diffractive structures incorporated in the light guide, in such a manner that the light exits predominantly to the side on which the operation of the device takes place. The dimensions of diffractive structures may also be especially in the nm range. In addition, the surface is designed such that the intensity distribution on the surface is essentially homogeneous. A corresponding touchscreen may, of course, also be fastened as a separate component at the edge of the lighting fixture for the operating room. The light coupled in can then take place either from a light source integrated in the component or by coupling in light of one of the light sources 3 of the lighting fixture for the operating room.

FIG. 3 schematically shows a supply unit for connecting a medical device. The supply unit 26 can be fastened on a ceiling, for example, via an articulated arm 22. At least one medical device, for example, a respirator for intensive care, can be connected to the supply unit 26 via a connection module 25. The supply unit provides a connection to a gas supply system and to electricity, for example, for a medical device connected via the connection module. As a control unit, the supply unit 26 has a handle 24 made of transparent plastic, which is hollow in its interior and is transilluminated with light of the wavelength of 405 nm by a light source 23. Furthermore, a touchscreen 13, which is coated with a control unit 15 on its rear side, is provided as a control unit, for example, for controlling a respirator connected to the connection module 25. To keep the touch surface 14 of the touchscreen 13 likewise as free from pathogenic bacteria as possible, an additional light source 16, which emits light especially at 405 nm and is directed towards the surface 14, is arranged on the supply unit 26 by means of a bracket 17. The surface 14 is thus illuminated by light of the wavelength of 405 nm, and pathogenic bacteria present on it are killed.

Furthermore, the supply unit 26 has a touchscreen 18 made of glass, which is used, for example, to actuate motors preset in the articulated arm 22 and thus to position the supply unit 26. The additional touchscreen 18 has a control unit 20 on its rear side. The touchscreen 18 is designed as a light guide made of glass, and light of the wavelength of 405 nm, which is emitted by an additional light source 21, is coupled into it. This light is reflected to and fro in the touchscreen 18 between a surface 19 and the control electrode 20, and it exits at least partially via the surface 19. Pathogenic bacteria present on the surface 19 are killed by the light exiting via the surface 19.

A surface structure, not shown in the figure, for example, an array of Fresnel structures designed in the mm or μm range, which surface structure reflects the coupled-in light specifically in the direction of the surface 19, so that light coupled in exits predominantly through the surface 19, is preferably formed on the control electrode 20. All other sides defining the touchscreen, with the exception of the surface 19, especially preferably have a reflecting coating. As an alternative or in addition, scattering, refracting or diffracting structures are incorporated in the light guide and are designed and arranged such that coupled-in light is guided predominantly in the direction of the surface 19, so that it will predominantly exit there. To facilitate the decoupling of the light reaching the surface 19, the surface 19 may have a refractive coating.

The light sources 16, 21 and 23 have the same design as the light sources 3, for example, especially in terms of their radiation sources and their spectra.

The supply unit 26 is additionally also designed as a medical device and has, for example, a defibrillator, not shown in FIG. 3 for clarity's sake. Additional medical devices may, of course, likewise be integrated directly in the supply unit 26.

Control units, i.e., handles and touchscreens as well as other, touch sensor-equipped control surfaces of medical devices, for example, anesthesia apparatuses, respirators and incubators, may, of course, also be advantageously illuminated and/or transilluminated by light sources that emit light with a central wavelength between 380 nm and 420 nm, especially at 405 nm.

LIST OF REFERENCE NUMBERS

1 Lighting fixture for an operating room
1' Surface
2 Control unit
3, 3' Light source
4, 4' Touch surface
5, 5' Touch sensor
6 Handle
7 Module
8 Lighting means
9 Optical system
10 Wall
11 Wall
12 Wall
13 Touchscreen
14 Touch surface
15 Control electrode
16 Light source 17 Bracket
18 Touchscreen
19 Touch surface
20 Control electrode
21 Light source
22 Articulated arm
23 Light source
24 Handle
25 Connection module
26 Supply unit

The invention claimed is:

1. A device for a medical treatment room, the device comprising
a control unit comprising a control unit surface;
a light guide defining at least a portion of the control unit surface; and
a light source, which light source emits light with a wavelength between 380 nm and 420 nm, and is arranged in such a manner that emitted light from the light source is coupled into the light guide, wherein the light guide is designed in such a manner that light exiting the light guide at least partially transilluminates the control unit surface of the control unit.

2. A device in accordance with claim 1, wherein the light guide comprises one or more light-guiding structures that are designed and arranged in the light guide and/or on surfaces thereof in such a manner that coupled-in light is guided in the direction of the surface of the control unit.

3. A device in accordance with claim 1, wherein the control unit comprises a handle.

4. A device in accordance with claim 1, wherein the control unit comprises at least one touch surface, which is in functional connection with a touch sensor and which is designed and/or arranged such that the touch surface is transilluminated by the emitted light when the light source is activated.

5. A device in accordance with claim 4, wherein the touch surface is at least partially made of transparent plastic or glass.

6. A device in accordance with claim 1, wherein the control unit comprises a touchscreen.

7. A device in accordance with claim 1, wherein the device is a lighting fixture for an operating room.

8. A device in accordance with claim 1, wherein the device is a supply unit for connecting a medical device.

9. A device in accordance with claim 1, wherein the device is a medical device.

10. A device in accordance with claim 1, wherein the light source emits light with a wavelength of about 405 nm.

11. A device in accordance with claim 1, wherein
said light guide being arranged to pass the light from said light source from inside said light guide through said control surface.

12. A medical arrangement in accordance with claim 11, wherein:
said light source and said control surface are arranged to have the light from said light source illuminate said control surface while said control surface operates said medical device.

13. A medical device comprising a control unit comprising:
a control unit surface;
a light guide defining at least a portion of the control unit surface; and
a light source emitting light with a wavelength between 380 nm and 420 nm, the light source being coupled with the light guide and the light guide configured to transilluminate the control unit surface of the control unit with the light emitted from the light guide.

14. A medical device in accordance with claim 13, wherein the light guide comprises one or more light-guiding structures positioned at least one of in an interior of the light guide and on surfaces of the light guide and guiding the light in a direction of the surface of the control unit.

15. A medical device in accordance with claim 13, wherein the control unit comprises:
a touch sensor;
a touch surface in functional connection with the touch sensor, the touch surface being configured such that the touch surface is transilluminated by the emitted light when the light source is activated.

16. A medical device in accordance with claim 13, wherein the device comprises a supply unit for supplying a medical device that is connectable thereto.

17. A medical device in accordance with claim 13, wherein the light source emits light with a wavelength of about 405 nm.

18. A medical device in accordance with claim 13, wherein
said light guide being arranged to pass the light from said light source from inside said light guide through said control surface.

19. A medical arrangement comprising:
a medical device;
a light source arranged one of in and on said medical device, said light source emitting light with a wavelength between 380 nm and 420 nm;
a light guide receiving the light from said light source;
a control surface on said medical device for operating said medical device, said control surface being arranged as a surface of said light guide, said light guide being arranged to pass the light from said light source from inside said light guide through said control surface.

20. A medical arrangement in accordance with claim 19, wherein:
said medical device performs a separate medical function that is different and separate from said light source, said control surface selectively controlling said separate medical function.

21. A medical arrangement in accordance with claim 20, wherein:
said control surface controls said medical device by being touched by an operator.

22. A medical arrangement in accordance with claim 19, wherein:
said light source illuminates said control surface with the light for a predetermined time during and after an operator has touched said control surface.

* * * * *